United States Patent [19]

Hashimoto et al.

[11] 3,941,823

[45] Mar. 2, 1976

[54] METHOD FOR PRODUCING ISONITROSOMALONIC ESTERS

[75] Inventors: Naoto Hashimoto; Masaaki Kuritani; Noriaki Toukai, all of Osaka, Japan

[73] Assignee: Takeda Chemical Industries, Ltd., Japan

[22] Filed: Oct. 18, 1973

[21] Appl. No.: 407,628

[30] Foreign Application Priority Data
Oct. 24, 1972 Japan.............................. 47-106472

[52] U.S. Cl.... 260/455 R; 260/112.5 R; 260/453 R; 260/482 P
[51] Int. Cl.²......................................... C07C 153/09
[58] Field of Search.......... 260/455 R, 453 R, 482 P

[56] References Cited
UNITED STATES PATENTS

| 3,301,883 | 1/1967 | Gruber............................ 260/453 R |
|---|---|---|
| 3,317,582 | 5/1967 | Tishler............................. 260/453 R |
| 3,492,375 | 1/1970 | Gruber et al..................... 260/455 R |
| 3,625,987 | 12/1971 | Hubele............................. 260/455 R |

OTHER PUBLICATIONS

Roger et al., "Chemistry of Imidotes" (1960) Chem. Rev. 61, p. 191 (1961).
Roger et al., "Chemistry of Imidotes" (1960) Chem. Rev. Vol. 61, p. 203 (1961).
Allenstein et al., "Addition Products of Hydrogen Halides etc., " (1964) CA61, p. 8187 (1964).

*Primary Examiner*—Glennon H. Hollrah
*Attorney, Agent, or Firm*—Wenderoth, Lind & Ponack

[57] ABSTRACT

Isonitrosomalonic acid esters, which are useful as a starting material for synthesizing sweet peptides and other chemicals, are prepared by allowing a nitrosating agent to act on a corresponding alkyl alkoxycarbonyl acetoimidate.

11 Claims, No Drawings

METHOD FOR PRODUCING ISONITROSOMALONIC ESTERS

The present invention relates to a method for producing isonitrosomalonic acid esters.

Isonitrosomalonic acid esters are converted to the corresponding aminomalonic acid esters by reduction of the former compounds, and the aminomalonic acid esters are useful as starting materials for the synthesis of various pharmaceuticals, agricultural chemicals and amino acid, particularly sweet peptides.

The isonitrosomalonic acid esters have been produced by nitrosating the corresponding malonic acid esters. It has become clear, however, that this method meets with an increasing difficulty with the increasing carbon number and volume of the alkyl moieties of the alkyl ester groups and that the nitrosation yield in this method is very poor, e.g. around 30 %. Further, when the two alkyl moieties of the two alkyl ester groups are different from each other, an additional difficulty is encountered in obtaining the asymmetrical starting material needed. Thus, this method is not advantageous from an industrial point of view.

The present inventors have made extensive studies for providing an industrially feasible method for the production of isonitrosomalonic acid esters, and have found out that reaction of an alcohol or mercaptan with a cyanoacetic acid ester or malonitrile can give the corresponding alkyl alkoxycarbonyl acetoimidate or malondiimidate, and found out that nitrosation of the alkyl alkoxycarbonyl acetoimidate or malondiimidate can give the desired isonitrosomalonic acid ester in very high yield, i.e. about 70 to about 90 % or higher, almost irrespective of the type and the molecular volume of the alkyl moieties of the alkyl ester groups.

The present invention has been completed on the basis of the foregoing findings.

Thus, the essential and principal object of the present invention is to provide a method for producing isonitrosomalonic acid ester in high yields.

The method of the present invention comprises reacting a compound of the general formula of

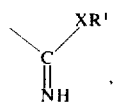  (I)

wherein
B is —COOR¹ or

X is O or S, R and R¹ are, same or different, alkyls which are unsubstituted or substituted by lower alkoxy or halogen,
with a nitrosating agent to give a compound of the following general formula (II), which is the object compound of the present invention;

  (II)

wherein the symbols have the same meaning as defined above.

The alkyl shown by the symbols R and R¹ may be straight chained, branched or cyclic. The carbon number of the alkyls is up to 20.

The halogen, the substitutent on the alkyl, includes chlorine, iodine, bromine and fluorine. The alkoxy, the substitutent on the alkyl, is lower one having carbon atoms of 1 to 4. Typical examples of the alkoxy are methoxy, ethoxy, propoxy, butoxy, etc. Typical examples of the substituted or unsubstituted alkyls are, among others, methyl, ethyl, n-propyl, isopropyl, n-butyl, sec.-butyl, t-butyl, n-amly, isoamyl, n-heptyl, n-hexyl, n-octyl, 2-ethylhexyl, n-nonyl, n-decyl, n-dodecyl, cyclobutyl, cyclopentyl, cyclohexyl, trans- or cis-2-methylcyclohexyl, mentyl, bornyl, isobornyl, adamantyl, 2-methoxy ethyl, 2-chloroethyl, 2-bromoethyl, 2-fluoroethyl, 2,2,2-trifluoroethyl, 2,2,3,3,3-pentafluoro-n-propyl, 2-chloro-n-propyl, 3-chloro-n-propyl, tridecyl, myristyl, pentadecyl, heptadecyl, stearyl, nonadecyl, eicosyl, etc.

The method of this invention is particularly advantageous in comparison with known methods, when the alkyl shown by R and that shown by R¹ are different from each other, or when both alkyls are the same with each other and they have three or more carbon atoms, i.e. propyl or higher.

The compounds of the formula (I), the starting material of the present method, may be free form or a salt with an anion such as chlorine ion, bromine ion, sulfhydryl ion, tetrafluoroboric ion, tetraphenylboric ion, methanesulfuric ion, etc.

The nitrosating agent employable in this method includes, for example, sodium nitrite, alkyl nitrite (e.g. ethyl nitrite, isoamyl nitrite, tertiary butyl nitrite, etc.), nitrosonium salts (e.g. nitrosonium tetrafluoroborate, etc.), dinitrogen tetraoxide, nitrosyl chloride, etc.

It is sufficient to employ said nitrosating agent in an amount corresponding to the sum of one molecular equivalent for the nitrosation of the methylene group of the compound (I) and one molecular equivalent per imidate or thioimidate group of

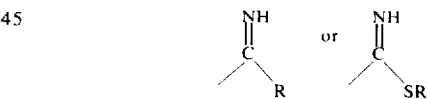

The reaction proceeds advantageously in a solvent, which may more commonly be acetic acid, dilute acetic acid, a mixture of acetic acid and hydrochloric acid, dilute hydrochloric acid, dilute sulfuric acid, dilute phosphoric acid and so on. If required, it is good practice to add an organic solvent such as, for example, chloroform, ethyl acetate or benzene to these solvents. The reaction can be conducted under cooling up to room temperature. Temperatures as high as will cause a thermal decomposition of the carboxy (thio) imidate group should be avoided. When dilute acetic acid is used as a reaction solvent, the reaction can be expediently performed at a temperature of from a few degrees to ten and odd degrees centigrade. After the reaction has been completed, the reaction mixture can be directly subjected to the subsequent procedure. Alternatively, it may be extracted with, for example, chloroform, ethyl acetate or benzene or the product may be isolated as an inorganic salt with, for example, silver, sodium, potassium or calcium or a tertiary amine salt with, for example, trimethylamine, triethylamine, tripropylamine, triallylamine, tribenzylamine or triphenylamine. If the above extract is dehydrated and, then, the solvent is distilled off, the object compound (II) is obtained in a crude form. This may be purified by such procedures as distillation and chromatography.

The compound (II) thus obtained can be converted to the corresponding aminomalonic acid esters of the formula

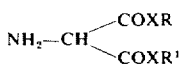

wherein X, R and R¹ have the same meaning as defined above, which are useful as starting materials for syntheses of various kinds of sweet peptides, e.g. L-aspartylaminomalonic acid diester derivatives (French Patent No. 7143535), or of other peptides, pharmaceuticals, agricultural chemicals, etc., by reduction of this compound. The reduction can be conducted after a conventional manner, catalytic reduction at atmospheric or elevated pressure in various solvents and in the presence of a catalyst such as platinum oxide, palladium or Raney nickel; the reduction method involving the combined use of an inorganic acid, e.g. dilute hydrochloric acid, dilute sulfuric acid or dilute phosphoric acid, and a metal such as zinc, iron or tin; the reduction method involving the combined use of an organic acid, e.g. acetic acid, and the above-mentioned metal; the reduction method involving the use of a chemical reducing agent such as sodium dithionite, sodium borohydride, sodium cyanoborohydride or the like under neutral or weakly acid conditions; and reduction method involving the use of amalgamated aluminum in a solvent such as an alcohol or aqueous ether. When the above reduction reaction is carried out in the presence of an acylating agent such as acetic anhydride, trifluoroacetic anhydride, acetic formic anhydride, the corresponding acylaminomalonic acid (thio) ester is obtained. Isolation of the product compound is performed, for example, by the distillation of the reaction mixture, by the addition of an equivalent amount of acid or by trimethylsilylation and subsequent hydrolysis. In this manner, the aminomalonic acid ester can be obtained in the free form or as an inorganic acid salt such as the corresponding sulfate, hydrochloride or hydrobromide or an organic acid salt such as the corresponding tartarate, oxalate, sulfonate, p-toluene-sulfonate or maleate.

The compound of the general formula (I), the starting material of this method can be prepared by reacting, as illustrated below, the corresponding cyanoacetic acid ester or malononitrile with the corresponding alcohol or thioalcohol;

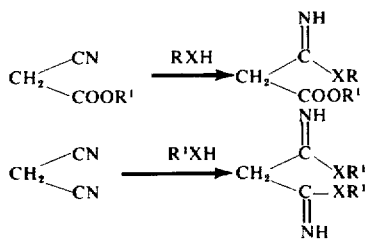

As to the proportion of said alcohol or thio-alcohol, from one molecular equivalent to 3 molecular equivalents of the same may be employed per cyano group of the starting material compound. This reaction is carried out in a solvent such as, for example, dry ether, chloroform, dioxane or benzene, though in many cases the reaction proceeds preferably in the absence of a solvent. In this connection, it is preferable to cause the solvent to absorb 1 to 3 molecular equivalents, preferably 1.4 to 1.5 molecular equivalents, of, say, dry hydrogen chloride gas or hydrogen bromide gas per cyano group of the starting material compound.

The reaction is preferably carried out at a temperature of from $-30°C$ to $35°C$ and, for better results, from $-10°$ to $25°C$. Though this compound can be isolated either as a free compound or as a salt with an anion such as chloride ion, bromide ion, sulfhydryl ion, tetrafluoroborate ion, tetraphenylborate ion, methanesulfate ion or the like, the reaction mixture as such may generally be used as a starting material in the subsequent nitrosation reaction.

In the following, working Examples are given for further explanation of the present invention.

In the Examples, "part(s)" means "weight part(s)", unless otherwise specified. The relation between "weight part(s)" and "volume part(s)" is the same as between "gram(s)" and "milliliter(s)."

EXAMPLE 1

Under cooling with ice, about 5 parts of dry hydrogen chloride gas was bubbled into a mixture of 11.3 parts of ethyl cyanoacetate and 4.6 parts of absolute ethanol. After the mixture was cooled with ice for a short while, it was allowed to stand at about 5°C overnight, whereupon colorless crystals of ethyl ethoxycarbonylacetoimidate hydrochloride were obtained in quantitative yield. This product was dissolved in 100 volume parts of acetic acid and, then, a solution of 13.8 parts of sodium nitrite in 25 volume parts of water was added over a period of about 7 to 10 minutes, at first at 14°–16°C and then at 5°–12°C. After the addition has been completed, the mixture was stirred at 18°–23°C for about 1 hour or until the evolution of nitrogen gas had completely subsided and the color of the reaction mixture had turned from purplish red to light yellow. Thereafter, about 500 volume parts of water was added and the mixture was extracted with ethyl acetate. The extract was washed with water and then with an aqueous solution of sodium hydrogen carbonate to remove the acetic acid. The organic layer was dehydrated over sodium sulfate and the solvent was distilled off the yield 19.0 parts of diethyl isonitrosomalonate as a viscous yellowish brown oil.

IR(pure liquid, $cm^{-1}$): 3330 (broad), 1750–1715(-broad), 1633, 1325, 1300, 1255, 1174, 1100, 1020, 858, 828, 770.

NMR (in deuteriochloroform, δ ppm): 1.32 (triplet, J=7Hz) and 1.33 (tripplet, J=7Hz) (total: 6H), 4.36(quintet, J=7Hz) and 4.40 (quintet, J=7Hz) (total=4H), 10.57(1H)

The above crude product was dissolved in a mixture of 79 volume parts of acetic acid, 25 volume parts of acetic anhydride and 3.5 volume parts of carbon tetrachloride and, under stirring, 27 parts of zinc dust was added at a temperature not exceeding 45°C. After the addition had been completed, the mixture was stirred at room temperature for 20 minutes and, then, the zinc dust was filtered off. To the filtrate was added 10 volume parts of water, followed by stirring for 30 minutes. The mixture was then extracted with chloroform and the extract was washed with water, dehydrated and distilled to remove the solvent. The resultant crystalline residue was recrystallized from water to yield a total of 19.6 parts of colorless crystals of diethyl acetamidomalonate. Yield 90.0 %.

EXAMPLE 2

Under cooling with ice, about 5 parts of dry hydrogen chloride gas was bubbled into a mixture of 11.3 parts of ethyl cyanoacetate and 10.0 parts of cyclohexanol. The mixture was then allowed to stand at about 5°C for 2 days, whereupon colorless crystals of cyclohexyl ethoxycarbonylacetoimidate hydrochloride were obtained in quantitative yield. This crystalline product was dissolved in 100 volume parts of acetic acid and treated or made to react with 13.8 parts of sodium nitrite in the same manner as Example 1. The procedure yielded 25.5 parts of crude isonitrosomalonic acid ethyl cyclohexyl diester.

IR(pure liquid, cm$^{-1}$): 3350(broad), 1740–1720(broad), 1637, 1260(broad), 1174(weak), 1160(weak), 1097, 1030(shoulder), 1007, 928, 905, 892, 860, 827

NMR(in deuteriochloroform, δ ppm): 1.13–2.18(broad, multiplet, with dominant peaks at 1.13, 1.22, 1.23, 1.25, 1.33, 1.35, 1.42 and 1.47; total 13H), 3.95–4.75(an absorption band with peaks at 3.95, 4.06, 4.18, 4.28, 4.32, 4.38, 4.43, 4.50, 4.55, 4.65 and 4.75; 2H), 500(broad, 1H), 10.45(broad, 1H).

The above product was dissolved in 150 volume parts of methanol and the solution was charged into an autoclave. Then, 6.25 parts of moist 5 % palladium-on-activated carbon was added and the system was allowed to react in hydrogen atmosphere at an initial pressure of 100 kg./cm$^2$ and at a temperature of 17°–25°C. When the pressure of hydrogen had dropped to near 70 kg/cm$^2$ a fresh supply of hydrogen was charged into the autoclave until a pressure of 100 kg./cm$^2$ was reached. The reaction was allowed to proceed for 2 hours, after which time the catalyst was removed and the supernatant was concentrated. The concentrate was dissolved in water and adjusted to pH 3.5 by the addition of dilute hydrochloric acid. The solution was extracted with benzene and the benzene layer was discarded. The water layer was concentrated and, then, cooled, whereupon aminomalonic acid monoethyl monocyclohexyl ester hydrochloride was obtained as colorless crystals melting at 106°–110°C (decomp.). Yield 91 %.

| Elementary analysis (C$_{11}$H$_{20}$NO$_4$Cl) | | | |
|---|---|---|---|
| | C | H | N |
| Calcd. | 49.72 | 7.59 | 5.27 |
| Found | 49.81 | 7.21 | 5.60 |

IR(Nujol, cm$^{-1}$): 3250–1950(N$^+$H$_3$), 1760, 1745(shoulder) (c=o), 1575, 1515, 1277

NMR(in d$_6$-DMSO, δ ppm): 0.82–2.00(10H), 1.23(triplet, 3H, J=7Hz), 4.27(quintet, 2H, J=7Hz), 4.65–5.01 (broad, 1H), 4.94(singlet, 1H), 9.33(broad)

EXAMPLE 3

Under cooling with ice, 2.6 parts of dry hydrogen chloride gas was caused to be absorbed in a mixture of 4.96 parts of methyl cyanoacetate and 5.70 parts of trans-2-methylcyclohexanol to obtain a homogeneous clear solution. This solution was allowed to stand at a temperature of about 5°C for 48 to 72 hours. This fluid was dissolved in 20 volume parts of acetic acid and, under cooling with ice and stirring, a solution of 6.90 parts of sodium nitrite in 10 volume parts of water was added to the above acetic acid solution at 22°–24°C over a period of about 10 minutes. After the addition had been completed, the mixture was further stirred at 22°–24°C for about one hour. To the resultant reaction mixture was added 200 volume parts of water, followed by extraction with benzene. The extract was washed with water, dehydrated and distilled to remove the solvent, whereupon 11.5 parts (94.5 %) of crude isonitrosomalonic acid monomethyl mono(trans- 2-methyl) cyclohexyl ester was obtained.

IR(pure liquid, cm$^{-1}$): 3340, 1750-1720, 1630, 1445, 1335, 1270, 1193, 1101, 1025, 975, 910, 848, 815, 776, 724.

NMR(in deuteriochloroform, δ ppm): 0.87, 0.97, 0.93 and 1.03 (a couple of doublets, 3H), 0.68–2.3(broad multiplet, 7H), 3.88 and 3.90 (total: 3H), 4.64 (broad, 1H), 10.8, approx. (broad, 1H)

Ten parts of the above product was dissolved in 60 volume parts of methanol and, then, 2.5 parts of 5 % palladium/activated carbon was added. The reaction was allowed to take place under the same conditions as those described in Example 2, whereupon aminomalonic acid monomethyl mono-trans-2-methyl cyclohexyl ester hydrochloride was obtained as colorless crystals melting at 113°–115.5°C (decomp.). Yield 88 %.

| Elementary analysis (C$_{11}$H$_{20}$NO$_4$Cl) | | | |
|---|---|---|---|
| | C | H | N |
| Calcd. | 49.72 | 7.59 | 5.27 |
| Found | 49.62 | 7.74 | 5.23 |

NMR(in d$_6$-DMSO, δ ppm): 0.80, 0.85, 0.88 and 0.93(singlet, each; total: 3H), 0.80–2.20(multiplet, 9H), 3.77 (singlet, 3H), 4.45 (broad, 1H), 4.95(singlet, 1H), 9.50(broad, 3H)

EXAMPLE 4

A mixture of 4.96 parts of methyl cyanoacetate and 5.70 parts of cis-2-methylcyclohexanol was caused to absorb 2.6-2.8 parts of dry hydrogen chloride gas and the system was allowed to stand at a temperature of about 5°C for 66 hours. Then, the reaction was conducted in the same manner as Example 3 to obtain 9.20 parts (yield 75.8 %) of crude isonitrosomalonic acid monomethyl mono-(cis-2-methyl) cyclohexyl ester.

IR(pure liquid, cm$^{-1}$): 3325, 1760-1715, 1634, 1446, 1350, 1270, 1214, 1194, 1155, 1136, 1104, 1023, 970, 910, 871, 848, 808, 777, 740–710

NMR(in deuteriochloroform, δ ppm); 0.84, 0.94, 0.89 and 0.99(a couple of doublets, 3H), 1.00–2.22(broad, with a dominant peak at 1.48, 7H), 3.87 and 3.90 (total: 3H), 5.15(1H), 10.5, approx. (broad, 1H)

This product was further reacted in the same manner as Example 2 to obtain aminomalonic acid monomethyl mono(cis-2-methyl) cyclohexyl ester hydrochloride, m.p.123°–126°C (decomp.). Yield 70.5 %.

Elementary analysis ($C_{11}H_{20}NO_4Cl$)

|  | C | H | N |
|---|---|---|---|
| Calcd. | 49.72 | 7.59 | 5.27 |
| Found | 49.62 | 7.46 | 5.28 |

NMR(in $d_6$-DMSO, δ ppm): 0.74, 0.80, 0.84 and 0.90(singlet, each, total 3H), 1.13–2.03(multiplet, 9H), 3.78 (singlet, 3H), 4.85–5.13 (broad, 1H), 5.01(singlet, 1H), 9.50(broad, 3H)

EXAMPLE 5

A mixed solution of 10.0 parts of malonitrile and 30.2 parts of cyclohexanol in 60 volume parts of dry dioxane was saturated with dry hydrogen chloride gas under cooling with ice. The mixture was then allowed to stand in a refrigerator for 2 days. The crystals that had separated were harvested by filtration and washed with dry ether to obtain 40.8 parts (yield 79.7 %) of malondiimidic acid dicyclohexyl ester dihydrochloride. Six parts of this product was dissolved in 25 volume parts of acetic acid and a solution of 3.72 parts of sodium nitrite in 25 volume parts of water was added at 8°–14°C. The mixture was stirrd at 18°–23°C for 1 hour and, after the addition of water, extracted with ethyl acetate. The procedure yielded 5.97 parts of crude isonitrosomalonic acid dicyclohexyl ester.

IR(pure liquid, $cm^{-1}$): 3325, 1740–1720, 1630, 1260, 1194, 1158, 1097, 1030, 1003, 924, 904, 890, 860, 840, 822, 772, 730, 675.

NMR(in deuteriochloroform, δ ppm): 1.05–2.26(-broad multiplet, 20H), 5.03(broad, 2H), 10.2(1H)

The above ester was dissolved in 25 volume parts of acetic acid and 2.3 parts of zinc dust was added at 50°C over a period of 2 hours. Then, water was added and the unreacted zinc was filtered off. The filtrate was extracted with ethyl acetate and the extract was dehydrated and distilled to remove the solvent. The procedure yielded 3.57 parts of aminomalonic acid dicyclohexyl ester as a light-yellow oil. Yield 71.3 %.

IR(pure liquid, $cm^{-1}$): 3350, 3300, 1740 NMR (in $CDCl_3$, δ ppm): 1.30–2.07(multiplet, 21H), 5.0(broad, 4H). Trifluoroacetyl compound, m.p.46°–47°C Elementary analysis ($C_{17}H_{24}O_5NF_3$)

|  | C | H | N |
|---|---|---|---|
| Calcd. | 53.82 | 6.38 | 3.69 |
| Found | 53.90 | 6.43 | 3.46 |

IR(Nujol, $cm^{-1}$): 3300, 1760, 1725

EXAMPLE 6

Under cooling with ice, a mixed solution of 49.54 parts of methyl cyanoacetate and 45.09 parts of n-butyl-mercaptan in 50 volume parts of dry either was caused to absorb 22.8 parts of dry hydrogen chloride gas. The system was allowed to stand in a refrigerator overnight and the resultant colorless crystals were harvested by filtration. The procedure yielded 109.8 parts (97.2 %) of methoxycarbonylacetothioimidic acid (n-butyl) ester hydrochloride. 7.8 parts of this product was dissolved in 50 volume parts of acetic acid and while the solution was cooled with icewater and stirred, a solution of 4.75 parts of sodium nitrite in 15 volume parts of water was added dropwise over a period of 15 minutes. The mixture was further stirred at room temperature for 3 hours and 100 volume parts of water was added to the resultant reddish brown reaction mixture. It was then extracted with ethyl acetate and the extract washed with a 5 % aqueous solution of sodium hydrogen carbonate. The organic layer was washed with a saturated aqueous solution of sodium chloride, dehydrated and distilled to remove the solvent, whereupon 5.32 parts of crude isonitrosomalonic acid monomethyl mono-n-butylthio ester was obtained as a brown viscous oil. Yield 70.4 %.

In a mixture of 15 volume parts of acetic acid and 10 volume parts of acetic anhydride was dissolved 3.64 parts of the above product and, under stirring, 5.0 parts of zinc dust was added over 30 minutes under mild cooling at a temperature near room temperature. Then, the mixture was heated at 60°–70°C for 30 minutes, at the end of which time 80 volume parts of water was added. It was then extracted with ethyl ether and the extract was washed with water and a saturated aqueous solution of sodium chloride. After dehydration, the solvent was removed by distillation, whereupon 4.03 parts of 2-n-butylthiocarbonyl-2-acetamidoacetic acid methyl ester was obtained as a colorless oil. Yield 98.5 %.

Elementary analysis ($C_{10}H_{17}O_4NS$)

|  | C | H | N |
|---|---|---|---|
| Calcd. | 48.57 | 6.93 | 5.66 |
| Found | 48.46 | 7.01 | 5.45 |

IR(pure liquid, $cm^{-1}$): 3300, 1750, 1680. NMR(in $CDCl_3$, δ ppm): 0.88(triplet, J=8Hz, 3H), 1.50 (multiplet, 4H), 2.08(singlet, 3H), 2.90(triplet, J=8Hz, 2H), 3.77(singlet, 3H), 5.40(doublet, J=8Hz, 1H), 7.80(doublet, J=8Hz, 1H)

EXAMPLE 7

Dry hydrogen chloride was bubbled into a mixed solution of 29.73 parts of methyl cyanoacetate and 46.27 parts of borneol in 100 volume parts of dry ether to substantial saturation and the reaction mixture was allowed to stand in a refrigerator overnight. The crystals were then harvested by filtration. The procedure yielded 84.05 parts (96.4 %) of methoxycarbonylacetoimidic acid bornyl ester hydrochloride. 15.0 Parts of this product was dissolved in a mixture of 100 volume parts of acetic acid and 10 volume parts of water and under cooling with ice, a solution of 7.15 parts of sodium nitrite in 20 volume parts of water was added dropwise over a period of 30 minutes. The mixture was stirred at room temperature for 1 hour and, after the addition of water, was extracted with benzene. The extract was concentrated to recover 14.73 parts of crude isonitrosomalonic acid monomethyl monobornyl ester. A pale yellow oil. (Though it contained a small amount of acetic acid, the yield was almost quantitative).

IR spectrum(pure liquid, $cm^{-1}$): 3300, 1740, 1720, 1105. NMR spectrum(in deuteriochloroform, δ ppm): 9.03(singlet, 1H), 5.10(broad, 1H), 3.87(singlet, slightly broad, 3H), 2.60–0.90 (multiplet, 16H).

14.60 Parts of the above crude isonitroso-compound was dissolved in 80 volume parts of acetic acid and, then, 0.269 part of platinum oxide was added. The mixture was stirred in a hydrogen atmosphere at room temperature and atmospheric pressure, whereby about 1800 volume parts of hydrogen gas was absorbed in 1.5 hour. Then, 100 volume parts of 6N hydrochloric acid was added and the catalyst was removed. The filtrate was extracted with benzene and the water layer was concentrated, whereupon a colorless viscous oil was obtained. This oil was suspended in 100 volume parts of ether and 10.4 parts of triethylamine was added. The mixture was stirred and the triethylamine salt was filtered off. The filtrate was concentrated to recover 8.73 parts of a crude product, which was then purified by distillation under reduced pressure. The procedure yielded 7.00 parts of aminomalonic acid monomethyl monobornyl ester as a colorless oil boiling at 134°C/3 mmHg.

IR spectrum(pure liquid, cm$^{-1}$): 3350, 1755, 1740, 1590. NMR spectrum(in deuteriochloroform, δ ppm): 4.93(broad, 1H), 4.21(singlet, 1H), 3.77(singlet, 3H), 2.00 (singlet, 2H), 2.60–0.82(multiplet, with singlets assignable to methyl protons at 0.90, 0.87 and 0.82; 16H).

EXAMPLE 8

Under cooling with ice, a mixture of 4.95 parts of methyl cyanoacetate and 50 millimole parts of one of several alcohols was caused to absorb about 2.5 parts of dry hydrogen chloride gas and the system was allowed to stand in a refrigerator for 2 to 4 days. Then, the entire system was dissolved in 50 volume parts of acetic acid. Under stirring at 10°–14°C, a solution of 6.9 parts of sodium nitrite in 15 volume parts of water was added over a period of 10 minutes. After the addition had been completed, the mixture was stirred for 45–55 minutes, its temperature being allowed to increase gradually to room temperature (about 22°–23°C). To the resultant reaction mixture was added about 300 volume parts of water and the mixture was extracted with benzene or ethyl acetate. The extract was washed with water and then, with a saturated aqueous solution of sodium chloride and, after dehydration, the solvent was distilled off, whereupon a crude product of the corresponding isonitrosomalonic acid ester was obtained as a light-yellowish oil. 30 volume parts of this crude product was dissolved in 75 volume parts of acetic acid and 1.25 millimole part of platinum oxide was added. The system was stirred in hydrogen gas at atmospheric pressure, whereby a substantially stoichiometric amount of hydrogen gas was absorbed in about 1.5 hour. The reaction mixture was adjusted to pH about 3 with 4N hydrochloric acid and the catalyst was removed by filtration. The filtrate was concentrated and about 70 volume parts of water was added to the concentrate. The mixture was extracted with benzene once and the benzene layer was separated. The water layer was concentrated under reduced pressure and further dried in vacuo. Over the resultant viscous oil was layered about 50 volume parts of dry ether and 4 parts of triethylamine was added, followed by stirring.

The precipitated triethylamine hydrochloride was filtered off and the ether was distilled off from the filtrate. The resultant oil which has a faint yellowish orange color was distilled under reduced pressure to obtain the corresponding aminomalonic acid ester. The weights of the aminomalonic acid esters thus obtained and of their intermediates, as well as their physical constants, are tabulated below. The NMR spectra of these aminomalonic acid esters are also given below.

$$CH_2\begin{matrix}CN\\COOCH_3\end{matrix} + ROH \rightarrow CH_2\begin{matrix}C\overset{NH}{\underset{OR}{\diagdown}}\\COOCH_3\end{matrix} \rightarrow HON=C\begin{matrix}COOR\\COOCH_3\end{matrix} \rightarrow H_2N-CH\begin{matrix}COOR\\COOCH_3\end{matrix}$$
$$(a) \hspace{2cm} (b)$$

| No. | R | (a) parts | (b) parts | b.p. (mmHg) |
|---|---|---|---|---|
| 1 | n-Ethyl | 8.10 | 5.10 | 75–77°C (4.0) |
| 2 | n-Propyl | 8.32 | 7.56 | 76–77.5°C (3.0) |
| 3 | n-Methoxyethyl | 7.96 | 6.15 | 95–130°C* (4.5) |
| 4 | n-Butyl | 7.90 | 6.09 | 119.5–120°C (8.0) |
| 5 | i-Butyl | 8.19 | 6.09 | 97–98°C (5.5) |
| 6 | sec-Butyl | 7.27 | 6.09 | 94°C (5.0) |
| 7 | n-Amyl | 8.67 | 6.51 | 110°C (4.0) |
| 8 | n-Octyl | 9.94 | 7.77 | 130–130.5°C (5.0) |

*The oil bath temperature is given for this ester only.

NMR spectra (in deuteriochloroform, δ ppm):

1. Aminomalonic acid monomethylmonoethyl ester 1.28(triplet, J=7Hz, 3H), 2.62(singlet, 2H), 3.77 (singlet, 3H), 4.20(singlet, 1H), 4.23(quartet, J=7Hz, 2H).

2. Aminomalonic acid monomethyl mono-n-propyl ester; 0.95(triplet, J=7Hz, 3H), 1.69(sextet, J=7Hz, 2H), 2.75(broad, singlet, 2H), 3.77(singlet, 3H), 4.15(triplet, J=7Hz, 2H), 4.21(singlet, 1H)

3. Aminomalonic acid monomethyl mono(2-methoxy)ethyl ester: 2.40(singlet, 2H), 3.35(singlet, 3H), 3.52–4.40(multiplet, 4H), 3.77(singlet, 3H), 4.25(singlet, 1H)

4. Aminomalonic acid monomethyl mono-n-butyl ester: 0.67–2.13(multiplet, with a peak at 0.93, 7H), 2.82 (broad, singlet, 2H), 3.78(singlet, 3H), 4.19(triplet, J=6Hz, 2H), 4.21(singlet, 1H).

5. Aminomalonic acid monomethyl mono-i-butyl ester: 0.93 (doublet, J=6.5 Hz, 6H), 1.97(multiplet, 1H), 2.41(singlet, 2H), 3.77(singlet, 3H), 3.97(doublet, J=7Hz, 2H), 4.22(singlet, 1H).

6. Aminomalonic acid monomethyl mono-sec-butyl ester: 0.88(triplet, J=7Hz, 2H), 4.23(double doublet, $J_1$=6.5 Hz, $J_2$≈ 1Hz, 3H), 1.63(quintet, J=7Hz, 2H), 3.03 (singlet, 2H), 3.77(singlet, 3H), 4.18(singlet, 1H), 4.90(sextet, J≈ 7Hz, 1H).

7. Aminomalonic acid monomethyl mono-n-amyl ester: 0.63–1.98(multiplet, with a peak at 0.91, 9H), 2.21 (singlet, 2H), 3.78(singlet, 3H), 4.18 (triplet, J≈6.5Hz, 2H), 4.20(singlet, 1H).

8. Aminomalonic acid monomethyl mono-n-octyl ester: 0.51–2,00(broad, multiplet, with a peak for methyl at 1.03 and dominant peak at 1.28, 15H), 2.22(singlet, 2H), 3.74(singlet, 3H), 4.17(triplet, J=6.5, 2H), 4.18(singlet, 1H).

EXAMPLE 9

A mixture of 9.9 parts of methylcyanoacetate and 8.05 parts of epichlorohydrin was saturated with dry hydrogen chloride gas under ice-cooling and further cooled with icewater for one hour, followed by keeping in a refrigerator overnight. The resulting solid was washed with ethylether and dried to give 19.9 parts of 2-chloroethyl methoxycarbonylacetimidate hydrochloride. Yield 92% Melting point: 103 to 107°C (decomposition).

NMR (in $d_6$-DMSO, $\delta$ppm): 3.72 (singlet, 3H), 3.97 (approx. triplet, J=5.6Hz, 2H), 4.8 (approx. triplet, J=5.6Hz, 2H), 11.2 (broad) and other complex absorption bands.

19.7 parts of the resultant was dissolved in 100 volume parts of acetic acid, and 13.8 parts of sodium nitrite in 30 volume parts of water was added to the solution over 10 minutes at 8° to 22°C, followed by stirring at 15° to 22°C for 1 hour. The resultant was diluted five times with water and extracted with ethyl acetate. The extract was washed with an aqueous sodium chloride solution, a 5% aqueous sodium bicarbonate solution and an aqueous sodium chloride solution in this order and dried over magnesium sulfate. Removal of the solvent gave 16.7 parts of isonitrosomalonic acid monomethyl mono-2-chloroethyl ester as a pale yellow oil. Yield: 86.5%

6.28 parts of the oil was dissolved in a mixture of 14.4 parts of acetic acid and 6.1 parts of acetic anhydride. To the solution was added 10 parts of zinc dust over 15 minutes at 10° to 45°C, followed by stirring for 20 minutes. The precipitates were taken out by filtration and washed with water. The filtrate and the washing water were combined and the solvent was removed under reduced pressure. The residue was recrystallized from acetonitrile-ethyl ether to give 4.59 parts of acetamidomalonic acid monomethyl mono-2-chloroethyl ester melting at 81° to 82°C. Yield: 65%

IR (Nujol mull, cm$^{-1}$): 3290, 1757, 1743, 1658, 1550, 1537, 1303, 1287, 1234, 1174, 1165, 1014, 980, 894, 764, 675. NMR (in CDCl$_3$, $\delta$ppm): 2.10 (singlet, 3H), 3.71 (approx. triplet, J≈6Hz, 2H), 3.85 (singlet, 3H), 4.48 (approx. triplet, J≈6Hz, 2H), 5.26 (doublet, J=7.2Hz, 1H), 6.65 (broad, doublet 1H).

EXAMPLE 10

In a similar manner to the Example 9, 22.2 parts of 2-bromoethyl methoxycarbonylacetimidate hydrochloride melting at 88° to 99°C (decomposition) was obtained from 9.9 parts of methyl cyanoacetate and 12.5 parts of epibromohydrin.

NMR (in $d_6$-DMSO, $\delta$ppm): 3.68 (singlet, 3H), 4.85 (approx. triplet, J≈5.6Hz, 2H), 11.2 (broad).

From 22.0 parts of the resultant, 13.8 parts of isonitrosomalonic acid monomethyl mono-2-bromoethyl ester was obtained in a similar manner to the Example 9. Pale yellow oil. Yield: 64%

From 7.62 parts of the resultant, 5.45 parts of acetamidomalonic acid monomethyl mono-2-bromoethyl ester was obtained in a similar manner to the Example 9. (recrystallization from acetonitrile-ethyl ether). Yield: 64%. Melting point: 84° to 85°C.

IR (Nujol mull, cm$^{-1}$): 3300, 1758, 1744, 1660, 1552, 1538, 1300 (sh), 1282, 1235, 1175, 1165, 1067, 985, 947, 896, 764, 680. NMR (in CDCl$_3$, $\delta$ppm): 2.08 (singlet, 3H), 3.53 (triplet, J=6Hz, 2H), 3.83 (singlet, 3H), 4.53 (approx. triplet, J=6Hz, 2H), 5.25 (doublet, J=7Hz, 1H), 6.66 (broad doublet, 1H)

EXAMPLE 11

In a mixture of 27.0 parts of stearyl alcohol in 200 volume parts of dry ethyl ether and 9.9 parts of methyl cyano acetate was introduced about 5.3 parts of dry hydrogen chloride gas at room temperature, followed by keeping at room temperature for 2 days. The resulting white precipitates were washed with ethylether and dried to give 19.0 parts of stearyl methoxycarbonylacetimidate hydrochloride melting at 83° to 85°C (decomposition). Yield: 46.8%

IR (Nujol mull, cm$^{-1}$): 3550–2550 (broad), 1758, 1670, 1578, 1472, 1294, 1246, 1168, 1115, 1027, 960, 910, 856, 721.

To 18.8 parts of the resultant suspended in 200 volume parts of acetic acid was added 6.9 parts of sodium nitrite in 15 volume parts of water over 30 minutes at 20°C. The resulting pale yellow suspension was agitated for one hour at room temperature, and to the suspension were added 500 volume parts of water and 250 volume parts of benzene to dissolve the solid material. The benzene layer was washed with an aqueous sodium chloride solution and dried over magnesium sulfate, and the solvent was removed to give 15.2 parts of crude isonitrosomalonic acid monomethyl monostearyl ester as amorphous colorless powder. Yield: 82%

6 parts of the resultant was dissolved in a mixture of 14.4 parts of acetic acid, 6.1 parts of acetic anhydride, 30 volume parts of benzene and 1 volume parts of carbon tetrachloride. To the solution was added 5.5 parts of zinc dust over 30 minutes at 25 to 35°C, followed by keeping at room temperature overnight.

The precipitates were removed by filtration and washed with benzne. The filtrate and the washings were combined and concentrated under reduced pressure. To the residue was added water, and the resulting white precipitates were washed with water, dried and recrystallized from acetonitrile to give 6.0 parts of acetamidomalonic monomethyl monostearyl ester melting at 75 to 77°C. Yield: 93.5%

IR (Nujol mull, cm$^{-1}$): 3300, 1757, 1744, 1660, 1648, 1553, 1537, 1352, 1277, 1237, 1073, 978, 890, 723. NMR (in CDCl$_3$, $\delta$ppm): 0.6–1.87 (a sharp peak at 1.25, and triplet at 0.88, J=6Hz, 35H), 2.08 (singlet, 3H) 3.78 (singlet, 3H), 4.20 (approx. triplet, J=6Hz, 2H), 5.18 (doublet, J=7Hz, 1H), 6.73 (broad, approx. doublet, 1H)

EXAMPLE 12

A solution of 3.0 parts of ethyl cyanoacetate and 2.66 parts of cyclohexanol in 6 volume parts of dry ethyl ether was substantially saturated with dry hydrogen chloride gas under cooling by an ice-salt bath, followed by keeping in a freezer overnight. The solvent was removed under reduced pressure, and the oily residue was dried at room temperature in vacuo. The resultant was washed with ethyl ether to give 6.45 parts of cyclohexylethoxycarbonyl acetimidate hydrochloride melting at 106° 107°C (decomposition). Yield: 97.0%

NMR (in CDCl$_3$, $\delta$ppm): 1.22–2.0 (broad multiplet, 10H). 1.32 (triplet, J=7Hz, 3H), 4.12 (singlet, 2H), 4.27 (doublet, J=7Hz, 2H), 5.33 (broad singlet, 1H), 12.40 (broad, about 2H)

18.0 parts of the resultant was suspended in 200 volume parts of dry ethyl ether, and to the suspension was added 7.23 parts of triethylamine, followed by agitation at room temperature for 30 minutes and further added 100 volume parts of water.

The ether layer was dried over magnesium sulfate and the ether was removed to give cyclohexylethoxycarbonylacetimidate as a colorless oil in a quantitative yield.

IR (liq. film, cm$^{-1}$): 3340, 3450, 1745, 1665, 1615.

In regard to the resultant, the following equilibrium was found to exist in a solution:

$$H_3CCH_2OOCCH_2C=NH \rightleftharpoons H_3CCH_2OOCCH=C-NH_2$$

A          B (in CDCl$_3$, A:B=35:65)

NMR (in CDCl$_3$, δppm):

A: 1.03–1.90 (multiplet, 10H), 1.27 (triplet, J=7Hz, 3H), 4.18 (quartet, J=7Hz, 2H), 4.18 (singlet, 2H), 4.90 (broad singlet, 1H), 7.78 (broad singlet, 1H)

B: 3.25 (singlet, 1H), 6.57 (broad singlet, 2H) and others.

What is claimed is:

1. A method for the production of a compound of the formula of $$HON=C\begin{matrix}\nearrow COXR \\ \searrow COXR^1\end{matrix} \qquad (II)$$

wherein X is O or S, R and R$^1$ are different from each other and represent a straight chain, branched or cyclic alkyl having up to 20 carbon atoms, which are unsubstituted or substituted by chlorine or bromine, which comprises reacting a compound of the formula:

$$\begin{matrix} NH \\ \parallel \\ CH_2 \diagdown C \diagup XR \\ \mid \\ B \end{matrix} \qquad (I)$$

wherein B is -COOR$^1$ or $$\begin{matrix} \diagdown \\ C-XR^1, \\ \mid \\ NH \end{matrix}$$

and X, R and R$^1$ have the same meaning as defined above, which a nitrosating agent in an amount at least equal to the sum of one molecular equivalent for the methylene group and one molecular equivalent per imidate or thioimidate group of the compound of the formula (I), said reaction being conducted with cooling or at room temperature, in a solvent.

2. A method as claimed in claim 1, wherein one of R and R$^1$ is methyl or ethyl and the other is cyclohexyl or 2-methylcyclohexyl.

3. A method as claimed in claim 2, wherein X is O.

4. A method as claimed in claim 2, wherein X is S.

5. A method as claimed in claim 2, wherein the nitrosating agent is sodium nitrite.

6. A method as claimed in claim 2, wherein R is 2-methylcyclohexyl.

7. A method as claimed in claim 2, wherein R is 2-methylcyclohexyl and R$^1$ is lower alkyl.

8. A method as claimed in claim 2, wherein R is 2-methylcyclohexyl and R$^1$ is methyl.

9. A method as claimed in claim 2, wherein the cyclic alkyl is cis-2-methyl-cyclohexyl.

10. A method as claimed in claim 2, wherein cyclic alkyl is trans-2-methyl-cyclohexyl.

11. A method according to claim 2 wherein the nitrosating agent is sodium nitrite, an C$_2$–C$_5$ alkyl nitrite, nitrosonium tetrafluoroborate, dinitrogen tetroxide or nitrosyl chloride.

* * * * *